United States Patent
Schwartz et al.

(10) Patent No.: US 6,690,180 B2
(45) Date of Patent: Feb. 10, 2004

(54) PROCESS AND APPARATUS FOR DETERMINING RATIO OF FLUID COMPONENTS SUCH AS METHANOL AND WATER FOR REFORMING FEED

(75) Inventors: Robert N. Schwartz, Costa Mesa, CA (US); Paul O. Braatz, Thousand Oaks, CA (US); Kevin W. Kirby, Calabasas Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 112 days.

(21) Appl. No.: 09/855,315

(22) Filed: May 15, 2001

(65) Prior Publication Data

US 2003/0016030 A1 Jan. 23, 2003

(51) Int. Cl.⁷ .................. G01R 27/26; G01N 33/20; G01N 30/62
(52) U.S. Cl. .................. 324/670; 324/690; 324/663; 324/676; 324/664; 324/687; 73/61.44; 73/61.61; 73/118.1
(58) Field of Search ................. 324/670, 690, 324/663, 676, 664, 687; 73/61.44, 61.61, 118.1, 61.43; 123/1 A

(56) References Cited

U.S. PATENT DOCUMENTS

| | | | |
|---|---|---|---|
| 3,114,262 A | * 12/1963 | Atun | 73/304 C |
| 3,420,753 A | 1/1969 | Happel et al. | 204/1 |
| 4,288,741 A | * 9/1981 | Dechene et al. | 324/664 |
| 4,426,616 A | * 1/1984 | Maier | 324/658 |

(List continued on next page.)

FOREIGN PATENT DOCUMENTS

WO    WO 01/13451 A1    2/2001

OTHER PUBLICATIONS

Abstract of JP 02–073145, *Patent Abstracts of Japan*, vol. 014, No. 264 (Jun. 7, 1990).

Abstract of JP 11–352089, *Patent Abstracts of Japan*, vol. 2000, No. 03 (Mar. 30, 2000).

Aricò, A.S., et al., "Optimization of operating parameters of a direct methanol fuel cell and physico–chemical investigation of catalyst–electrolyte interface," *Electrochemica Acta*, vol. 43, No. 24, pp 3719–3729 (1998).

"Research and Development of Proton–Exchange–Membrane (PEM) Fuel Cell System for Transportation Applications," *U.S. Department of Energy Report*, DOE/CH/10435–02 (Jan. 1996).

Perry, Robert H., *Chemical Engineers' Handbook*, Fifth Edition, pp. 22/51–21/52 (1969).

Dean, John A. (ed.), *Lange's Handbook of Chemistry*, Thirteenth Edtition, pp. 10–95, 10–96, 10–99, 10–100, 10–101, and 10–110 (1985).

*Primary Examiner*—Stephen R. Funk
*Assistant Examiner*—Wasseem H. Hamdan
(74) *Attorney, Agent, or Firm*—Ladas & Parry

(57) ABSTRACT

A method and sensor for determining the ratio of two components in a fluid mixture comprising a test cell in open communication with the fluid mixture and a reference cell containing a desired fluid mixture not in contact with the fluid mixture being tested, said reference and test cells having the same cell geometry. By use of a capacitance divider system, one determines the relative capacitances of said cells correlated with the dielectric constants of the respective fluid mixtures and ascertains the ratio of one component to the other component in the fluid mixture on the basis of the linear and monotonic correlation between the dielectric constant of the mixture at a given temperature and the ratio of one component to the other component. Preferably a mixture of methanol and water is tested such as for use as a feed to a reformer used in supplying hydrogen to a fuel cell. A fixed capacitor equivalent to the reference cell at a given temperature is usually substituted for the latter.

29 Claims, 7 Drawing Sheets

U.S. PATENT DOCUMENTS

| | | | | |
|---|---|---|---|---|
| 4,810,597 A | * | 3/1989 | Kumagai et al. | 429/22 |
| 4,924,702 A | * | 5/1990 | Park | 73/304 C |
| 4,939,468 A | * | 7/1990 | Takeuchi | 324/690 |
| 4,971,015 A | * | 11/1990 | Gonze | 123/494 |
| 5,005,402 A | * | 4/1991 | Pischinger et al. | 324/663 |
| 5,068,617 A | | 11/1991 | Reich | 324/663 |
| 5,124,655 A | * | 6/1992 | Takeuchi et al. | 324/690 |
| 5,255,656 A | * | 10/1993 | Rader et al. | 123/494 |
| 5,270,663 A | * | 12/1993 | Sano et al. | 324/676 |
| 5,594,163 A | * | 1/1997 | Suzuki | 73/61.44 |
| 5,801,307 A | * | 9/1998 | Netzer | 73/170.17 |
| 5,861,755 A | * | 1/1999 | Moerk et al. | 324/663 |
| 6,375,832 B1 | * | 4/2002 | Eliasson et al. | 208/141 |

* cited by examiner

PROCESS AND APPARATUS FOR DETERMINING RATIO OF FLUID COMPONENTS SUCH AS METHANOL AND WATER FOR REFORMING FEED

FIELD OF THE INVENTION

The present invention relates to a process and apparatus for determining the ratio of components in a fluid mixture, particularly a sensor for use in determining the ratio of water to methanol in a reforming feed for producing hydrogen for supply to a fuel cell system.

DESCRIPTION OF THE PRIOR ART

The use of fuel cells in electrically powered vehicles has become important for the purpose of reducing air pollution normally resulting from internal combustion engines. As a way of producing the hydrogen gas to be supplied to the fuel cell in combination with oxygen gas, usually supplied as the oxygen present in atmospheric air, it is known to supply a mixture of methanol and water to a catalytic reforming reactor to convert said mixture to carbon dioxide and hydrogen according to the endothermic reaction:

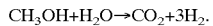

$CH_3OH + H_2O \rightarrow CO_2 + 3H_2$.

Such a system is described in the U.S. Department of Energy Report (DOE/CH/10435-02) of January 1996, entitled Research and Development of Proton-Exchange-Membrane (PEM) Fuel Cell System for Transportation Applications.

In order to operate such a reforming system it is important that the ratio of methanol to water in the reforming feed be continuously monitored and correspondingly controlled so that the optimum ratio of these reactants for the reforming reaction is achieved. The measurement of the ratio of methanol to water can be carried out by chromatography methods. However, such techniques used in the laboratory are not practical for industrial or commercial applications, such as for fuel cell systems in electrically powered vehicles or in electric power sources suitable for other purposes, such as in satellite communication devices and in stationary "home" power systems. In general it is desirable to have a sensor suitable for continuously measuring the ratio of components in fluids, both gases and liquids. Although it is useful to have a sensor measure the ratio of the methanol and water in the gas phase fed to the above reforming system, it is practical to measure the ratio of the methanol to water in the liquid phase in equilibrium with the gas phase mixture fed to the reformer.

It is known to use oscillometry for determining the water content of a liquid mixture since water has a dielectric constant fifteen to twenty times that of other substances (see PERRY, CHEMICAL ENGINEERS' HANDBOOK, FIFTH EDITION, 1969, PAGE 22–52). LANGE'S HANDBOOK, THIRTEENTH EDITION, 1985, cited below, discloses dielectric constants for a number of substances, including water and methanol.

SUMMARY OF THE INVENTION

It is an object of the present invention to provide a process for determining the ratio of methanol to water in a fluid mixture containing same.

Another object of the invention is to provide a sensor for determining the ratio of two components in a fluid mixture, particularly a liquid mixture, mixtures with different ratios of said components having respectively different dielectric constants at given conditions of frequency of an imposed alternating voltage and of temperature of said fluid mixture.

It is a further object of the invention to provide a sensor for determining the ratio of two gas components in a gas mixture, mixtures with different ratios of said components having respectively different dielectric constants at given conditions of frequency of an imposed alternating voltage and of temperature and pressure when said mixture is placed between opposed electrodes imposing said alternating voltage.

In accordance with one aspect of the present invention, there is provided a sensor for determining the ratio of two components in a test fluid mixture, mixtures with different ratios of said components having respectively different dielectric constants at a given frequency of an imposed alternating voltage and at a given temperature of said test fluid mixture when said test fluid mixture is subjected to said alternating voltage, said sensor comprising:

a first pair of opposed electrodes establishing there between a test cell, the opposed electrodes of said test cell being in contact with said test fluid mixture being tested, said test cell having a test cell impedance;

a reference cell established by a second pair of opposed electrodes having equivalent operating characteristics to those of the first pair of opposed electrodes, said reference cell containing a reference fluid mixture of the two components in a known ratio and being isolated from said test fluid mixture, said reference cell having a reference cell impedance;

an electrical circuit wherein one of the opposed electrodes of the first pair of electrodes is connected to one pole of a source of alternating voltage and one of the electrodes of the second pair of electrodes is connected to the other pole of the source of alternating voltage, and wherein the other of the opposed electrodes of the first and second pair of electrodes are connected together for serial flow between said pairs of electrodes of the test cell and reference cell, respectively; and a voltage measuring device connected to said circuit for measuring the voltage drop across the test cell so as to determine the voltage drop across the test cell in relation to the voltage drop across the reference cell;

said relative voltage drops being used to determine said test cell impedance relative to said reference cell impedance and thus to determine the dielectric constant of the test fluid mixture relative to that of the reference fluid mixture at a given temperature of said test and reference fluid mixtures and at,a given voltage of the imposed alternating voltage, whereby the ratio of said components of the test fluid mixture to the ratio of the components of the reference fluid mixture is correlated with the respective dielectric constants of said test and reference fluid mixtures.

In a modification of the sensor of the invention, representing a preferred embodiment, the reference cell is replaced by a reference element including a capacitor connected to the same source of alternating voltage as the first pair of electrodes, said reference element having a known impedance corresponding to that of such a (hypothetical) reference cell containing the reference fluid mixture of two components of a known ratio and at a specific temperature. In this embodiment, there is provided a temperature measuring device for measuring the temperature of the mixture in the test cell and a voltage measuring device (connected to the electrical circuit in which the reference element replaces the reference cell) for measuring the voltage drop across the test cell electrodes and across the reference element of known impedance so as to compare the respective impedances and determine the ratio of the two fluid components of the mixture in the test cell on the basis of the impedance of the fluid mixture in the test cell and the temperature of said fluid mixture.

In accordance with another aspect of the present invention there is provided a process for testing a fluid mixture containing methanol and water in a given ratio so as to determine said ratio, which comprises:

establishing a test cell between opposed, electrodes contacting said fluid mixture, said fluid mixture being tested at a given temperature and said test cell being in open flow communication with said fluid mixture being tested;

imposing an alternating voltage of a given frequency across said electrodes;

measuring the dielectric response of the fluid mixture in said test cell at said temperature and frequency, and determining the ratio of methanol to water in said mixture on the basis of the dielectric response thus measured.

In the usual practice of this above process the dielectric response of the test cell is measured in terms of the dielectric constant of the fluid mixture in said cell, the dielectric response of the fluid mixture being tested varying in an essentially linear and monotonic relation to the ratio of methanol to water in said mixture at a given temperature of said fluid.

The sensor provided by the present invention measures the dielectric response of the fluid mixture, such as a methanol/water mixture, in either liquid or vapor phases. The invention takes advantage of the properties of such fluid components to have a dielectric response, namely, dielectric constant, measured at low frequencies (corresponding to a static dielectric constant), which varies linearly and monotonically with the ratio of the concentration of one component to the concentration of the other component, usually expressed as the weight percent of one component to the total weight of both components. In particular, the present invention concerns determining the ratio of the concentration of methanol to the concentration of both methanol and water in a fluid mixture containing same, usually a fluid mixture consisting essentially of said components, preferably consisting of said components. In the usual practice of the invention the electrical circuitry of the sensor acts as a capacitance divider which allows measurement of the dielectric response of a fluid mixture of an unknown composition at any instant time relative to the dielectric response of a known composition, particularly a fluid mixture of methanol and water corresponding to a desired weight ratio of a specific value.

In the basic practice of the invention there is provided a reference cell which has opposed electrodes of equivalent operational characteristics, which may be termed "cell geometry", as the electrodes of the test cell, so as to facilitate the evaluation of the voltage drop or other operational characteristics of the test cell by comparison to the reference cell. Typically, the reference cell, except for the absence of the openings to the fluid in the enclosure, is identical in construction to the test cell. As will be described below, the reference cell participates in extending the dynamic range of the measurement of the dielectric constant, namely the capacitance, of the fluid mixture in the test cell. The reference cell is closed or isolated with respect to the fluid being measured whereas the test or sample cell is in open communication with the fluid in the enclosure so as to be in contact with said fluid. In the case of a liquid mixture, the electrodes of the test cell are preferably totally immersed in the liquid so that the total surface of the electrodes is in contact with the liquid mixture so as to insure a consistent area of contact with the liquid mixture for each test. Similarly, the opposed electrodes of the reference cell are preferably totally immersed in the liquid mixture in the reference cell. In one embodiment, both the outer walls of the test cell and of the reference cell are made of plastic with the edges of the opposed electrodes mounted in said walls. The reference cell and the test cell are in side-to-side relationship and separated by a common electrode. The outer electrodes of both cells are preferably in direct contact with the fluid being tested. Since the reference cell tends to be at substantially the same temperature as that of the test cell by virtue of the fact that the test cell and reference cell are both in heat exchange contact with the fluid mixture through the common electrode and the outer electrodes (even though the reference cell is not in fluid communication with the fluid being tested in the enclosure), the only variable is the difference in ratio between the two components of the fluid in the reference cell and the ratio of said components in the test cell. The fluid mixture of the reference cell has a ratio of methanol to water corresponding to a specific value for the mixture being measured in the test cell. In this way by comparative electrical circuitry used in the present invention it is possible to monitor the ratio of the mixture in the test cell so as to take steps to ensure that the ratio of the components of the fluid in the test cell, communicating with the fluid being sampled, is as close as possible to the desired ratio in the reference cell. Because of the greater heat transfer between outer walls of the cells and the fluid in the enclosure when the fluid is a liquid as opposed to a gas, the practice of the invention using a reference cell is of greater effectiveness when the mixture being measured is a liquid.

Determining the dielectric response of both the reference cell and the test cell is carried out by measuring the capacitance of both cells. Because of the equivalent operating characteristics of both cells and the substantially equal temperatures of the respective liquid mixtures one can determine the capacitance of the test cell as compared to that of the reference cell by appropriate measurements using the circuitry as described in greater detail herein. The difference in phase of the alternating voltage at the test cell and the reference cell is correlated with respect to the known static dielectric constants of various ratios of the mixture of methanol and water, or other components, at given temperatures and alternating current frequencies. The frequency of the applied voltage and temperature of the fluid mixtures of both the reference cell and the test cell are essentially the same so that the monotonic correlation between the ratio of these components and the dielectric constants of the mixtures in the respective cells (as a function of the capacitances of the fluid mixtures determined for said cells) can be utilized to effect a calculation of the ratio of the fluid components in the test cell by reference to "look-up" tables, correlating the linear and monotonic relationship of the static dielectric constants with various known ratios of the components as described above.

One can determine the phase difference between the test cell and the reference cell by current low-cost ADC circuitry. Matters can be simplified by choosing an alternating current frequency above the inverse of the bulk dielectric relaxation time expected for the fluid mixture being tested, in which event the complex impedances of both the reference and test cells reduce to simple capacitance calculations so that the determination can simply be that of the amplitude of the capacitance measured. 100 KHz is presently contemplated. The applied voltage is typically in the order of 10 millivolts.

The electrodes of the test cell as well as the corresponding reference cell are usually in the form of parallel plates or coaxial cylinders.

In the practice of a process aspect of the present invention instead of a reference cell containing a mixture of methanol and water of a known ratio, usually a desired ratio, and at a specific temperature corresponding to the temperature of the fluid of the test cell, one can use a fixed and stable capacitor of given capacitance or impedance corresponding to such a (hypothetical) reference cell. Typically the capacitor corresponds to a reference cell which is identical to the test cell. According to this aspect, it is necessary to measure the temperature of the test cell and compare the impedance or capacitance of the test cell to that of the reference capacitor so as to determine the capacitance of the test cell. One then determines the ratio of methanol to water in the fluid mixture of the test cell on the basis of the capacitance thus determined (as converted to the dielectric constant) and the temperature of the mixture in the test cell. In this case the determination is based on a three-dimensional plot of dielectric constant for the fluid methanol/water mixture as a function of composition and temperature, as is further discussed below. Corresponding "look-up" tables containing these parameters as incorporated in suitable software can be utilized to carry out the computation of the mixture ratios corresponding to the two-dimensional and three-dimensional look-up tables noted above.

In utilizing the process and sensor of the present invention in determining the ratio of components in a gas mixture, one must take into account the pressure of the mixture in the test cell as compared to that in the reference cell since the dielectric constant of the gas mixture is also a function of the pressure of a gas. The pressure variation can be used to adjust the calculation of the ratio of the gas component by taking into account the known relationship in the LANGE handbook noted below. Since an actual reference cell, in which the pressure (and possibly the temperature) must also be measured, is generally not practical for the gas embodiment, the practice of the invention in which the fluid mixture being measured is a gas mixture is usually carried out by providing a reference element of given impedance, said impedance being equivalent to that of a (hypothetical) reference cell having equivalent operating characteristics to those of the test cell, said reference cell having a gas mixture of methanol and water of a known ratio and of a known temperature and pressure and being operated at the same frequency as that of the test cell. The practice of the invention then includes:

measuring the temperature and pressure of the gas mixture being tested, measuring the impedance of the gas mixture in the test cell, comparing the impedance of the test cell to that of the reference element so as to determine the capacitance of the test cell, and determining the ratio of methanol to water in the test cell on the basis of the capacitance, temperature and pressure of the gas mixture in the test cell.

Other objects and advantages of the present invention will become apparent to those skilled in the art from the following description read in conjunction with the attached drawings and claims appended hereto.

DETAILED DESCRIPTION OF THE INVENTION

Figure 1:
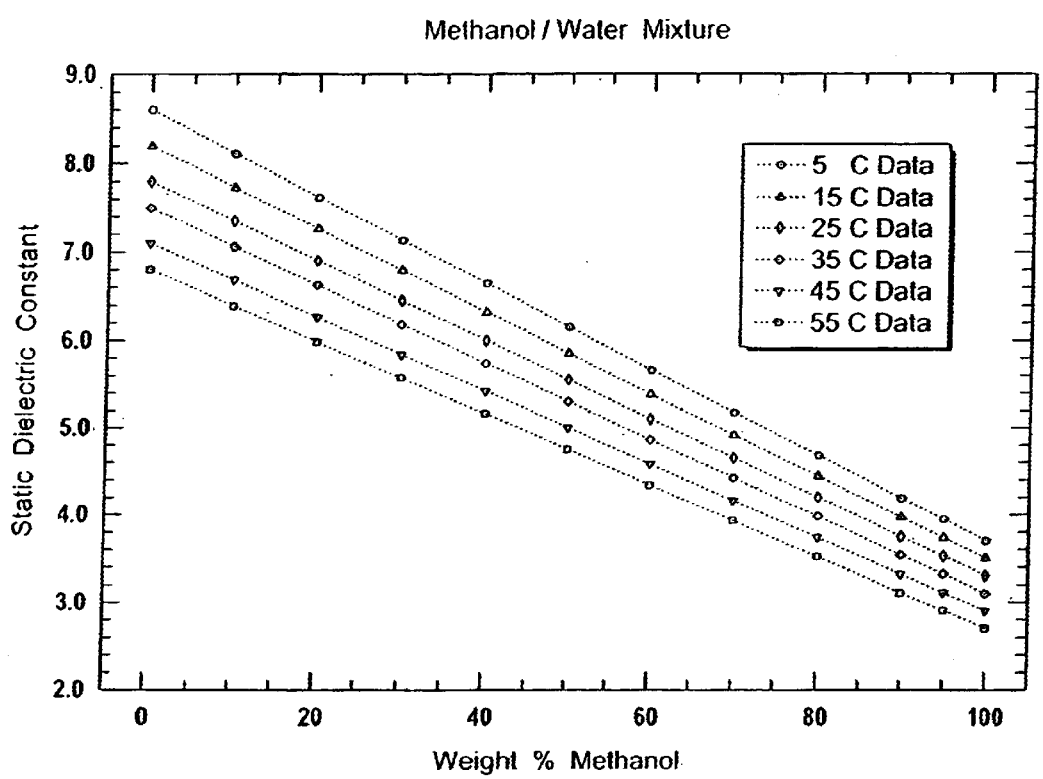
FIG. 1 shows the dielectric constants for known methanol/water liquid mixtures as a function of the weight percent of methanol in the mixture at various temperatures.

The underlying principle of the method and apparatus of the present invention is the direct correlation on essentially a linear and monotonic basis between the dielectric response of a fluid mixture of two components as a function of the weight of one component in the mixture to the weight of that component with the other component. This correlation is of particular value in measuring the weight percentage of methanol in a mixture of methanol and water at various temperatures. FIG. 1 shows the correlation between the low frequency dielectric response, namely the dielectric constant, and the weight percentage of methanol in a methanol/water liquid mixture at various temperatures as indicated. FIG. 1 clearly shows a linear and monotonic decrease in dielectric response with increased weight percent of methanol. The "static dielectric constant" indicated in FIG. 1 is measured in a frequency range above the inverse of the dielectric relaxation time but below the optical dielectric frequency of the liquid mixture. Although FIG. 1 shows the relationship for a liquid phase composition, a similar behavior is applicable to vapor phase (gas) mixtures at a given pressure.

To present the data of FIG. 1 in most specific form, there follows a table corresponding to the data shown in FIG. 1 in which the weight percentages of methanol in the water/methanol mixture are given more specifically.

| Temp., C. | Wt. % 10 | Wt. % 20 | Wt. % 30 | Wt. % 40 | Wt. % 50 | Wt. % 60 | Wt. % 70 | Wt. % 80 | Wt. % 90 |
|---|---|---|---|---|---|---|---|---|---|
| 0  5.0000 | 81.680 | 77.380 | 72.800 | 67.910 | 62.960 | 57.920 | 52.960 | 48.010 | 42.900 |
| 1 15.000 | 77.830 | 73.590 | 69.050 | 64.310 | 59.540 | 54.710 | 49.970 | 45.240 | 40.330 |
| 2 25.000 | 74.180 | 69.990 | 65.550 | 60.940 | 56.280 | 51.670 | 47.110 | 42.600 | 37.910 |
| 3 35.000 | 70.680 | 66.520 | 62.200 | 57.700 | 53.210 | 48.760 | 44.420 | 40.080 | 35.650 |
| 4 45.000 | 67.320 | 63.240 | 58.970 | 54.620 | 50.290 | 46.020 | 41.830 | 37.700 | 33.530 |
| 5 55.000 | 64.080 | 60.060 | 55.929 | 51.690 | 47.530 | 43.420 | 39.380 | 35.460 | 31.530 |

Figure 2B:
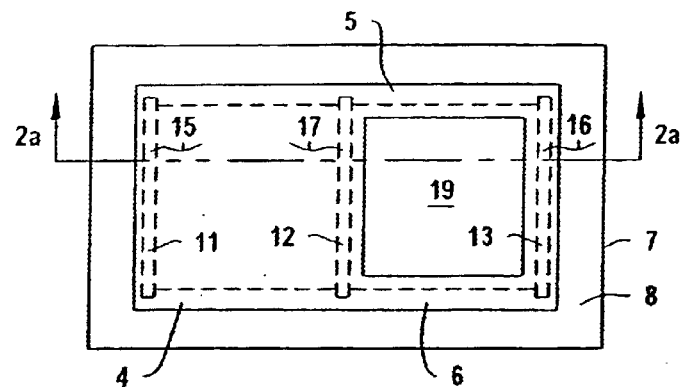
FIG. 2b is a plan view taken from above of the sensor shown in FIG. 2a, and showing electrodes and interior wall surfaces (hidden from view) by dashed lines.
Figures 2A, 2C:
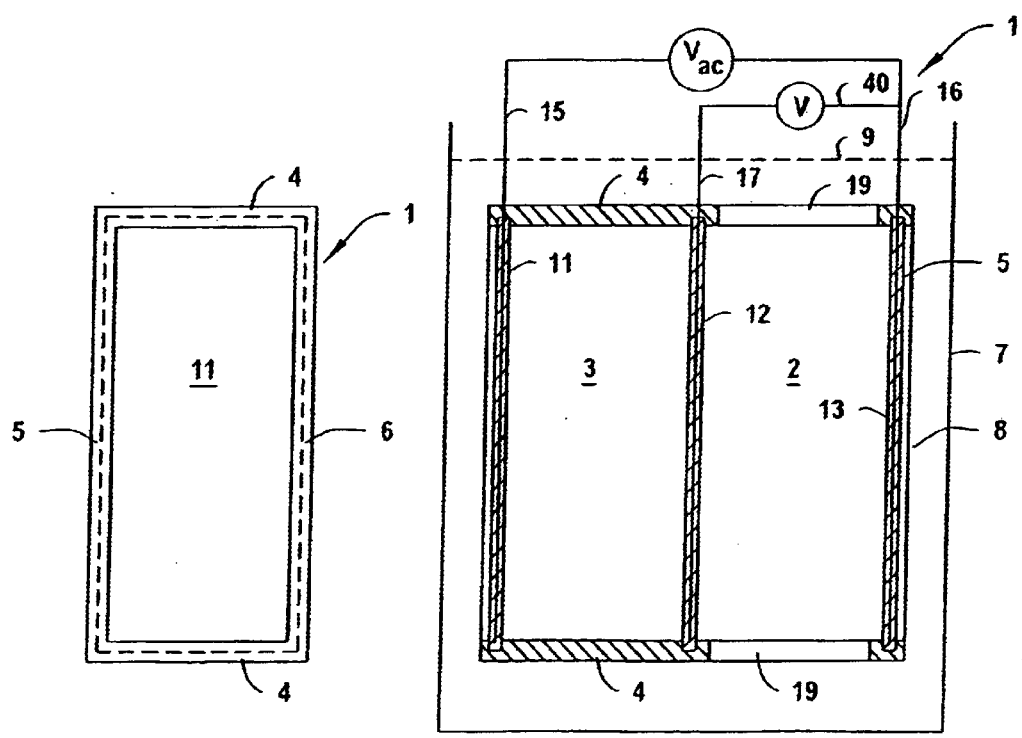
FIG. 2a is a vertical cross-sectional view in the direction of 2a—2a of FIG. 2b of a sensor according to the present invention submerged in a liquid being tested and showing the presence of both the reference cell and sample cell.
FIG. 2c is an end view, from the left, of the combination of cells shown in FIG. 2a, and showing the periphery of the electrodes, embedded in the walls, by dashed lines.

FIGS. 2a, 2b and 2c illustrate a basic embodiment of the apparatus for measuring the dielectric response of a methanol/water fluid mixture 8 contained in an enclosure 7. In this embodiment, a sensor 1, consists of two separate compartments 2 and 3. One, compartment 3, serves as a reference cell, which is sealed and contains as a reference composition a methanol/water mixture of fixed and known composition. The other compartment 2 serves as a test cell. The reference composition is chosen to be one that is near the optimum value required for efficient operation of a methanol/water mixture for feed to a reforming system, which in turn produces hydrogen for supply to a fuel cell for generating electricity. Typically 43.5 wt. % methanol is present in a liquid mixture consisting of methanol and water.

Compartments 2 and 3 are defined by top and bottom walls 4, 4' and side walls 5, 6 made of molded plastic, such as polyethylene, of one-eighth inch thickness, and opposed electrodes 11, 12, 13 made of stainless steel (or other inert metal). A common electrode 12 is centrally portioned between the other two outer electrodes 11, 13 so as to divide the sensor into compartments 2 and 3. The electrodes 11, 12, 13 are embedded adjacent their edges in the top and bottom walls 4, 4' and the side walls 5, 6, so as to be maintained in parallel relationship to each other with the spacing between electrodes 11, 12 the same as that between electrodes 12, 13. FIG. 2c shows the exterior of electrode 11 of the reference compartment 3 as opposed to the liquid bath 8 being tested in enclosure 7. The view of the interior surface of electrode 11, of both exposed surfaces of common electrode 12, and of the interior and exterior surfaces of electrode 13 of the test compartment 2 are each the same as the exposed surface of electrode 11 shown in FIG. 2c. In any event, it is necessary that the areas of exposure of the surfaces of electrodes 11, 12, 13 facing the reference and test compartments 3, 2 and the spacings of parallel opposing electrodes of said respective compartments 3, 2 are the same so that reference cell or compartment 3 and the test cell or compartment 2 have the same operating characteristics or "cell geometry."

To permit test compartment 2 to be in open-flow communication with the methanol-water mixture 8 being tested, the regions of top and bottom walls 4, 4' in the test compartment 2 between electrodes 12 and 13 are provided with top and bottom openings 19, 19', respectively. There are no openings in the regions of top and bottom walls 4, 4' (nor in the regions of the side walls 5, 6) defining reference cell 3. Nevertheless, the liquids in the test and reference cell compartments 2, 3 are both maintained at substantially the same temperature by virtue of the indirect heat exchange which occurs between the liquid bath 8 and the liquid within reference compartment 3 through electrode 11, as well as between test compartment 1 and reference compartment 3 through common electrode 12. Also, the top and bottom walls 4, 4' and the side walls 5, 6, made of plastic, also conduct heat to a certain extent. It is important that compartments or test and reference cells 2, 3 be at substantially the same temperature so that both cells lie nearly on the same data line as shown in FIG. 1, usually within 5.0° C., preferably within 1.0° C.

The opposed electrodes 11, 12, 13 have a rectangular shape of dimensions of 3 inches by 2 inches and a thickness of 0.02 inches and lie in parallel planes with the opposed surfaces spaced from each other one-quarter inch. Electrical leads 15, 16 extend from the outer electrodes 11, 13 of cell compartments 3 and 2, respectively, to connect said outer electrodes 13, 11 to opposite poles of a source of alternating voltage, $V_{ac}$. Common electrode 12 is connected through top wall 4 to electrical lead 17 for establishing voltage $V_x$, which as measured by voltage measuring device V, connected to lead 16 by electrical lead 40 and to common electrode 12 by electrical lead 17, is utilized as discussed below to ascertain relative capacitances of cell compartments 2 and 3. Electrical leads 15, 16 and 17 are contained in connectors, preferably coaxial connectors, such as Amphenol RG-174. Preferably, the entire exposed surfaces of electrodes 11, 12, 13 within the test cell 2 and the reference cell 3 are in contact with the liquid within the respective cell compartments so that the areas of surface contact between the electrodes and the fluid are constant and thus measurements between the respective electrodes and said cells are on a consistent basis. In the basic embodiment shown in FIGS. 2a and 2b, the fluid mixture being tested in the enclosure 7 is in the liquid phase and has an upper level 9 above the top of the electrodes 12, 13 of the test cell compartment 2 so that the electrodes of the test cell are completely submerged below the level 9 of the liquid mixture 8.

It will be noted that reference cell 3 and test cell 2 of FIGS. 2a, 2b, and 2c have equivalent operating characteristics by having the same cell geometries since the opposed electrodes 11, 12 and 12, 13 establishing said respective cells 3, 2 are made of the same respective materials and have the same internal dimensions and spacings.

Figure 3:
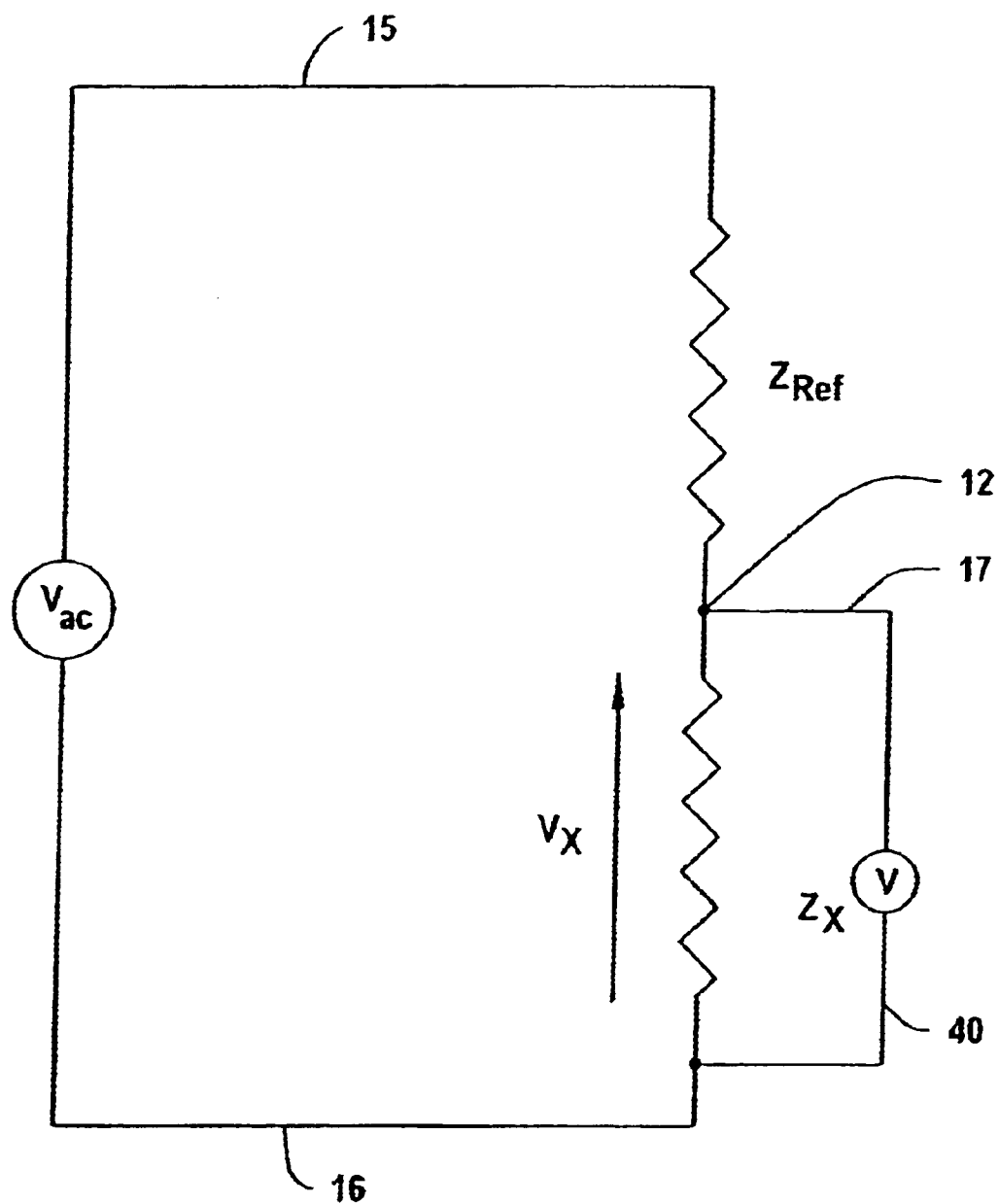
FIG. 3. shows the equivalent circuitry, schematically shown, for the sensor in FIGS. 2a and 2b.

FIG. 3 shows a circuit diagram for analyzing the impedances of the respective cells (ref=reference cell mixture and x represents test cell mixture) and incorporates the electrical leads 15, 16, 17 and 40, common electrode 12 (acting as a common junction), source of alternating voltage $V_{ac}$ and voltage measuring device V shown in FIG. 2a. Electrical lead 15 extends from the outer electrode of the reference cell of impedance $Z_{Ref}$ and is connected to one pole of alternating voltage source $V_{ac}$ and electrical lead 16 connects the outer electrode of test cell of impedance $Z_x$ to the other pole of alternating voltage source $V_{ac}$. The inner electrodes of the reference and test cells by virtue of being a common inner electrode 12 are connected to a common junction. This arrangement establishes serial flow between the opposed electrodes 13, 12 of test cell 2 and the opposed electrodes 11, 12 of reference cell 3 as shown in FIG. 2a. Voltage measuring device V is connected by electrical lead 17 to common junction 12 and by electrical lead 40 to electrical lead 16. In this way voltage measuring device V bridges test cell 2 and measures the voltage drop across said cell.

Figure 4:
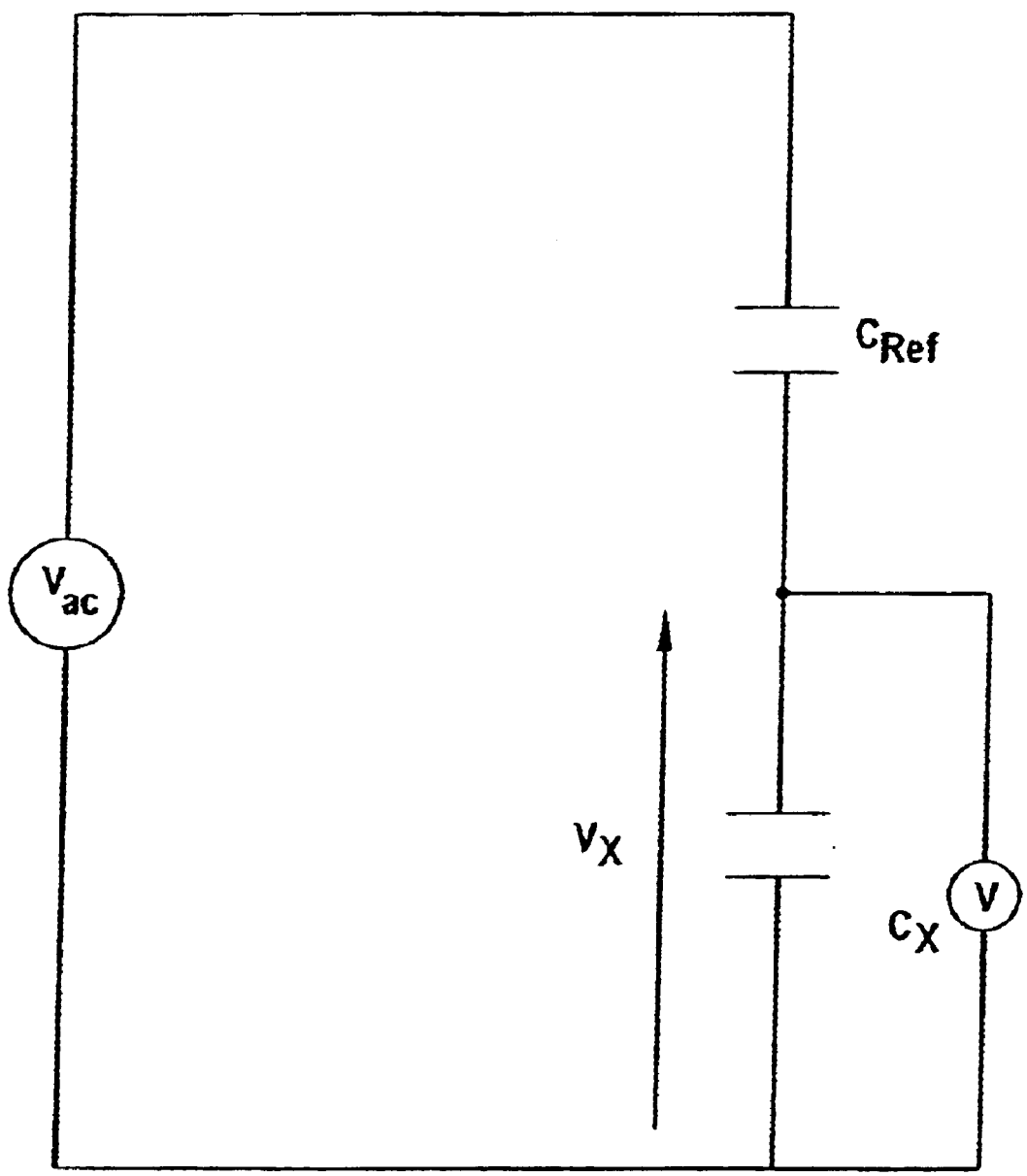
FIG. 4. corresponds to FIG. 3. showing a simplification of the circuitry of FIG. 3., in which the respective impedances of the test cell and reference cell are reduced to simple capacitors so that a simple amplitude-sensitive detection method can be utilized.

In general the impedances of the test and reference cells are complex, each consisting of both real and imaginary components. To measure the capacitive component at any frequency, which is proportional to the dielectric constant of the unknown mixture, one measures both the amplitude (as measured by voltmeter V) and phase of $V_x$ relative to $V_{ac}$. Such a measurement generally requires some type of phase/sensitive detection scheme, such as with current low-cost ADC circuitry. However, as shown with reference to FIG. 4, one choosing an operating frequency above the inverse of the bulk dielectric relaxation time can simplify the complex impedance of both the reference and test cells to simple capacitances. FIG. 4 shows the equivalent circuit under such circumstances to that depicted in FIG. 3. Therefore, working above the inverse of the bulk dielectric relaxation time has the advantage in that a simple amplitude-sensitive detection method can be utilized.

If one operates under such circumstances, and following mathematical manipulation and simplification, the ratio of the alternating voltage source to the voltage drop across the test cell has the following simple form.

$$\frac{V_{ac}}{V_x} = 1 + K_{CellGeometry}\left[\frac{\varepsilon_x(\rho_x, T)}{\varepsilon_o(\rho_o, T)}\right] \quad (1)$$

where $K_{Cell\ Geometry}$ is a fixed constant that is determined by the common geometry of the test and reference cells, $V_{ac}$ is the amplitude of the imposed voltage, $V_x$ is the amplitude of the voltage drop across the test cell, $\varepsilon_x$ is the dielectric constant of the mixture in the test cell, and $\varepsilon_0$ is the dielectric constant of the mixture in the reference cell. $\rho$ and $T$ represent the concentration (wt. %) of methanol and temperature of the mixtures respectively. Let us now assume that the concentration-dependent dielectric response can be expressed by $$\varepsilon_x(\rho_x, T) = \varepsilon_o(\rho_o, T) + \varepsilon'(\rho_o, T)[\rho_x - \rho_o], \quad (2)$$

where $$\varepsilon'(\rho_o, T) = \left[\frac{\partial \varepsilon_x}{\partial \rho}\right]_{\rho_o, T}.$$

Substitution of Equation (2) into Equation (1) yields an approximate expression for unknown mixture concentration ratio $\rho_x$.

$$\rho_x = \rho_o + \gamma(\rho_o, T) \cdot \left[\frac{V_{ac}}{V_x} - 2\right], \quad \text{where} \quad (3)$$

$$\gamma(\rho_o, T) = \left[\frac{\varepsilon_o(\rho_o, T)}{\varepsilon'(\rho_o T)}\right]. \quad (4)$$

Utilizing a simple first-order approximation for the temperature dependence of $\varepsilon_o(\rho_o, T)$ and $\varepsilon'(\rho_o, T)$ one obtains:

$$\varepsilon_0(\rho_0, T) = \varepsilon_0(\rho_0, T_0)[1 + \alpha(\rho_0, T_0)(T - T_0)] \quad (5)$$

and $$\varepsilon'(\rho_o, T) = \varepsilon'(\rho_o, T_o)[1 + \beta(\rho_o, T_o)(T - T_o)]. \quad (6)$$

Substituting Equations (5) and (6) into Equation (4) yields:

$$\gamma(\rho_o, T) = \gamma(\rho_o, T_o)\left\{\frac{[1 + \alpha(\rho_o, T_o)\Delta T]}{[1 + \beta(\rho_o, T_o)\Delta T]}\right\}, \quad \text{where} \quad (7)$$

$$\alpha(\rho_o, T_o) = \frac{\left(\frac{\partial \varepsilon_o}{\partial T}\right)_{\rho_o, T_o}}{\varepsilon_o(\rho_o, T_o)} \quad (8)$$

$$\beta(\rho_o, T_o) = \frac{\left(\frac{\partial \varepsilon_x}{\partial T}\right)_{\rho_o, T_o}}{\left(\frac{\partial \varepsilon_x}{\partial \rho}\right)_{\rho_o, T_o}} \quad (9)$$

We now proceed to evaluate $\alpha(\rho_o, T_o)$ and $\beta(\rho_o, T_o)$ using the known experimental data. We choose $\rho_o$=43.5 wt. % methanol, which corresponds to {[water]/[methanol]}$_{optimum}$=1.3. For $T_o$ we arbitrarily choose 35° C. From the experimental data, we obtain:

$$\left(\frac{\partial \varepsilon_o/\partial T}{\partial T}\right)_{\rho_o, T_o} = -0.318 \text{ and } \varepsilon_o(\rho_o, T_o) = 56.3.$$

This yields a value for $\alpha(\rho_o, T_o) = -5.6 \times 10^{-3}$. For $\beta(\rho_o, T_o)$, we obtain from the experimental data:

$$\left(\frac{\partial \varepsilon_o/\partial T}{\partial T}\right)_{\rho_o, T_o} = -0.318 \text{ and } \left(\frac{\partial \varepsilon_x/\partial \rho}{\partial \rho}\right)_{\rho_o, T_o} = -0.441,$$

which yields $\beta(\rho_o, T_o) = 0.72$. For $\gamma(\rho_o, T)$, we thus obtain from Equation 7:

$$\gamma(\rho_o, T) \approx \gamma(\rho_o, T_o)\left[\frac{1}{(1 + 0.72\Delta T)}\right], \quad (10)$$

noting that $\gamma(\rho_o, T_o)$ is a constant that is determined by the known properties of the mixture at $\rho_o$ and $T_o$. This is a relatively simple formula for the temperature dependence of the measured quantity that can be accounted for by straightforward numerical algorithms. If the device described above is used in an environment in which the test cell and reference cell are maintained at substantially the same temperature, as in the preferred embodiment of FIGS. 2a and 2b, and/or with circulation of the fluid mixture and supply or removal of heat with thermostatic control, of the fluid being tested, then the term in square brackets in Equation 10 is a very close to unity.

Combining (3) and (10) we obtain the concentration of the mixture in the test cell:

$$\rho_x \approx \rho_o + \gamma(\rho_o, T_o)\left[\frac{1}{(1 + 0.72\Delta T)}\right] \cdot \left[\frac{V_{ac}}{V_x} - 2\right]. \quad (11)$$

When $\Delta T = 0$ equation (11) becomes a version of formula (3)

$$\rho_x \approx \rho_o + \gamma(\rho_o, T_o) \cdot \left[\frac{V_{ac}}{V_x} - 2\right]. \quad (12)$$

Therefore, from the measurement of $V_x$, the concentration of the mixture in the test cell $\rho_x$ can be calculated using equation (12) when $T_x = T_o$, $\rho_o$, $\gamma(\rho_o, T_o)$, and $V_{ac}$ all having known values.

In the case $\Delta T \neq 0$, the knowledge of the temperature of the test mixture relative to temperature of the reference mixture is needed, as shown by equation (11).

Figure 5:
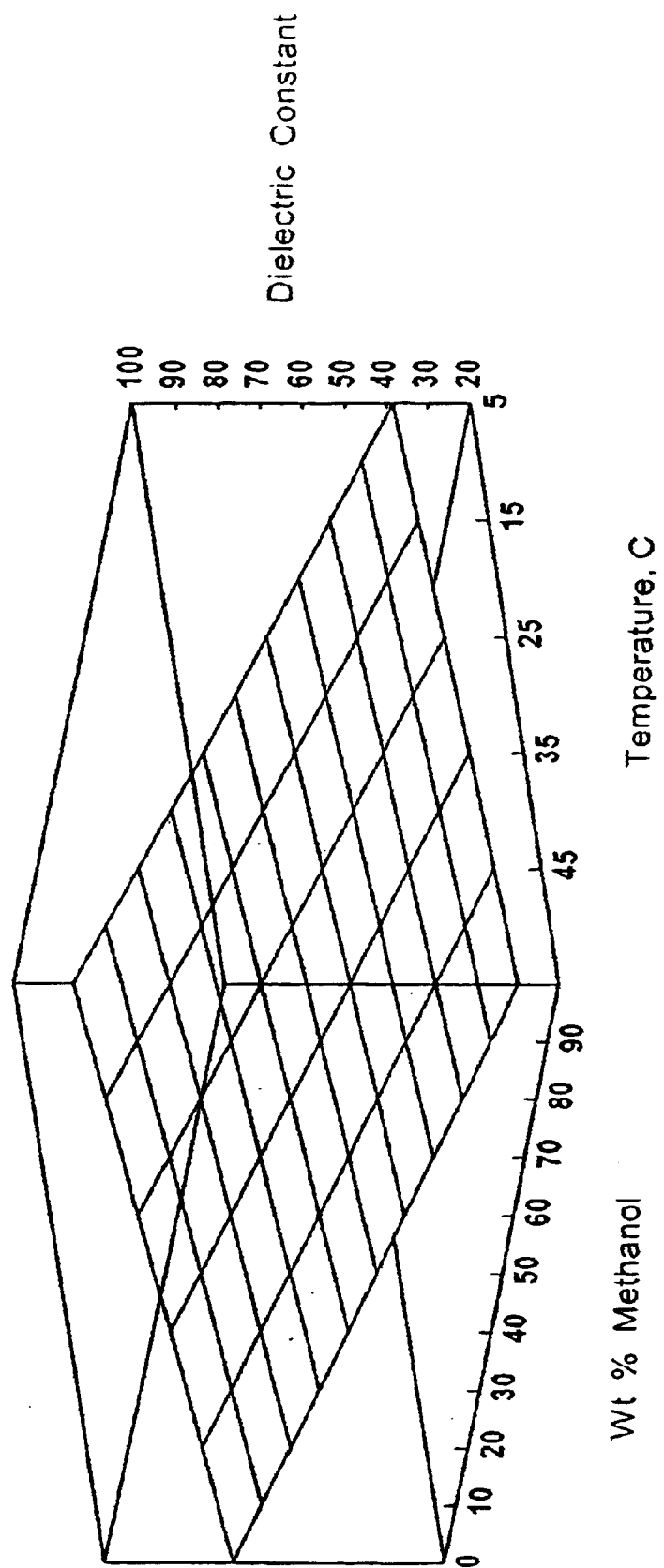
FIG. 5. shows a three dimensional plot of dielectric constants for liquid methanol/water mixtures of different ratios as a function of ratio and temperature.

It is possible to replace the $Z_{Ref}$ of FIG. 3 or $C_{Ref}$ of FIG. 4 with a reference element which is a fixed and stable capacitor of predetermined impedance, said impedance being the same as that of a hypothetical cell corresponding to an actual reference cell $Z_{Ref}$ or $C_{Ref}$ as described above. Such an embodiment would have $Z_{Ref}$ in FIG. 3 or $C_{Ref}$ in FIG. 4 substituted by such a fixed and stable capacitor. In this way one can measure the unknown capacitance of the test cell from which the dielectric constant can be obtained without the need to construct and maintain a reference cell. This approach requires one to use the 3-dimensional plot of dielectric constant for liquid methanol/water mixtures as a function of composition and temperature as shown in FIG. 5. Below are expressions for the dielectric constant as a function of composition p and temperature T obtained by a least-squares fit to the experimental data illustrated in FIG. 5:

$\in(\rho,T) = 85.9839 - 0.449561\,\rho - 0.289117 T.$ (linear)

$\in(\rho,T) = 86.0568 - 0.425749\rho - 0.000231\,\rho^2 - 0.332492 T + 0.000723 T^2.$ (quadratic)

In the event that pressure must be measured in the embodiment where a gas mixture is measured, there would be a number of such three dimensional plots, each plot corresponding to a different pressure, and one correlates the dielectric constant for the mixture as a function of the composition and temperature at each such pressure.

Figure 6:
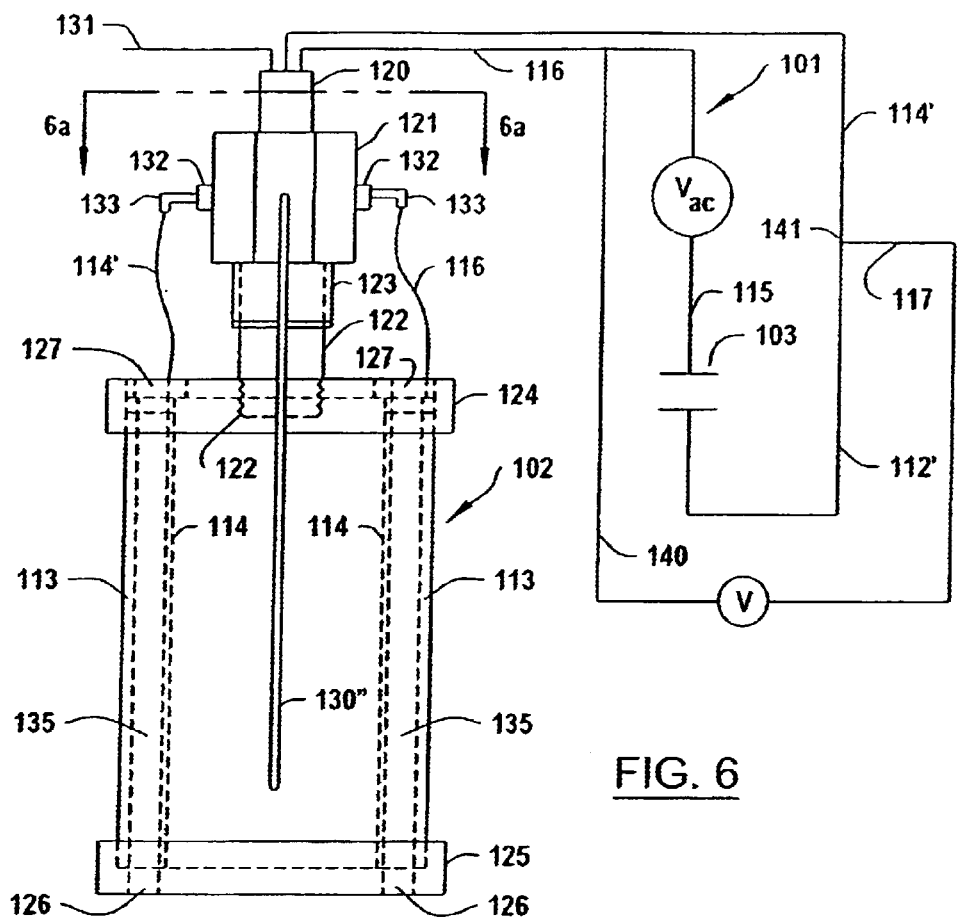
FIG. 6. shows a side view of a preferred embodiment of the test cell of the sensor of the invention including coaxial cylindrical electrodes connected to a fixed capacitor of known impedance serving as a reference cell.
Figure 6A:
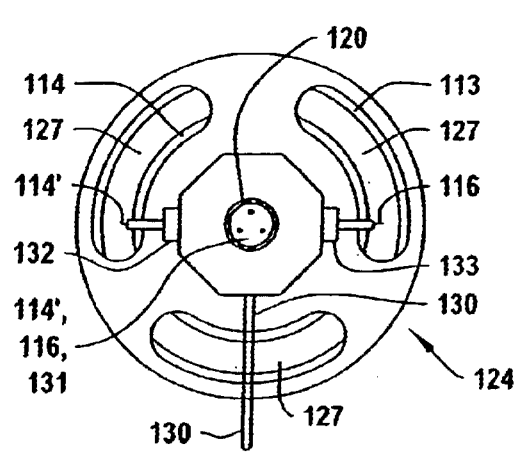
FIG. 6a. is a horizontal cross-sectional view in the direction of 6a—6a of the test cell shown in FIG. 6.

The sensor 101 shown in FIG. 6 represents a prototype of a preferred embodiment of the invention, in which coaxial test cell 102 is used in conjunction with a fixed capacitor 103 of known impedance corresponding to a hypothetical test cell having a mixture of methanol and water at a given temperature and of a desired ratio, usually expressed as the weight ratio of the methanol to the methanol and water mixture. The test cell 102 includes an outer cylindrical electrode 113 and an inner cylindrical electrode 114, both made of stainless steel of 0.02 inches thickness with an outside diameter of 1.5 inches for inner cylindrical electrode 114 and an outer diameter of 2 inches for outer cylindrical electrode 113. Both electrodes 113, 114 have a height of 3 inches and are rigidly mounted between an upper plastic mounting ring 124 and a lower plastic mounting ring 125, so as to maintain a uniform radial distance between the opposing surfaces of electrodes 113, 114. The entire length of the inner surface of outer electrode 113 faces the entire length of the outer surface of inner electrode 114. The upper mounting ring includes openings 127, as shown in FIG. 6a, which openings 127 have sufficient radial width to expose the upper edges of the electrodes 113, 114 to provide connection to electrical leads 116 and 114' as will be described below. Sufficient plastic material of upper ring 124 lies between the circumferential ends of openings 127 so that the plastic material of the intervening plastic portions between adjacent holes 127 maintains the upper edges of the electrodes 113, 114 in firm contact with the upper ring 124. On the other hand, the holes 126 of lower ring 125 extend to a much longer circumferential distance and are separated by narrow bridges 129. The holes 127 and 126 permit substantial fluid communication with the fluid mixture in the enclosure (not shown). As in the embodiment of FIGS. 2a, 2b, and 2c the sensor 102 is submerged below the liquid level in the enclosure (in the event that a liquid is being tested). Cylindrical electrodes 113, 114 are thus radially spaced from each other by respective electrically insulating means in the form of plastic mounting rings 123, 124 adjacent opposite ends of said cylindrical electrodes to form annular space 135 for the flow of fluid tested in the enclosure.

The electrical leads 114' and 116 are contained in an electrical housing 121, which is supported by a mounting hollow rod 120. The upper mounting ring 124 is connected to the housing 121 by connecting rod 122, which includes a threaded portion 122', which is screwingly engaged with the interior of the central portion of the plastic ring 124, which extends across the entire width of said ring 124, except for the openings 127. Connecting rod 122 is fastened to electrical housing 121 by means of tightening nut 123. Rod 120 thus supports sensor 102.

Also extending from electrical housing 121 with a radial leg 130' so as to extend outboard of said test cell 102 is a temperature probe 130, which includes a downwardly extending leg 130" parallel to and outboard of the outer cylincrical electrode 113. Said temperature probe 130 is connected to temperature probe output circuit 131. The electrical leads 114' and 116 extend from right angle plugs 133, which are connectable to electrical jacks 132, positioned in said electrical housing and connecting with the electrical leads 116, 114', extending outwardly of the top of the hollow rod 120. As in the embodiment of FIGS. 2a, 2b and 2c, the electrical leads 116 and 114', are contained in connectors, preferably coaxial electrical connectors, such as Amphenol RG-174. Electrical leads 116 and 114' are connected to one pole of the voltage source $V_{ac}$ and common junction 141, respectively. Voltage measuring device V is connected to common junction 141 by lead 117 and to lead 116 by lead 140 to measure the voltage drop across electrodes 113, 114. Reference element 103 of known impedance corresponding to that of a reference cell, containing a known methanol-water mixture at a given temperature and being identical to test cell 102 so as to have equivalent operating characteristics to that of the test cell 102, is connected at one side to the other pole of voltage source $V_{ac}$ by means of lead 115, with the electrical lead 112' connecting the other side of the reference element 103 to the common junction 141. The electrodes 113, 114 of test cell 102 are in series with reference element 103.

Figure 6B:
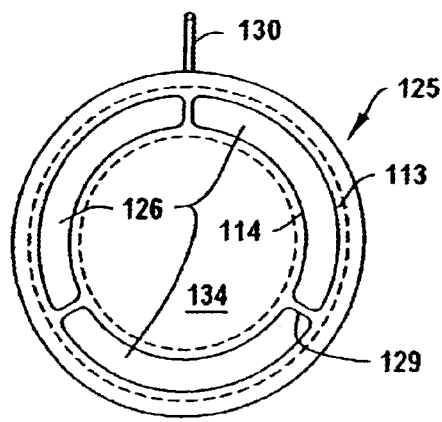
FIG. 6b. is a bottom view of the test cell shown in FIG. 6.

It should be noted that the lower ring 125 has a solid central portion extending between openings 126. The outer peripheral edges of the circular inner portion 134 of the lower ring 125 support the lower edges of inner cylindrical electrode 114 and the inner outer-ring portions of ring 125 support the lower edges of the outer cylindrical electrode 113. It should be noted that the inner surface of inner electrode 114 and the outer surface of cylindrical electrode 113 are shown by dashed line in FIG. 6b and that the inner surface of outer electrode 113 and the inner and outer surfaces of the inner electrode 114 are shown by dashed lines in FIG. 6. Dashed lines also show the continuation of connecting rod 122 inside of tightening nut 123, as well as the screw threads 122' of connecting rod 122 (engaging the center portion of upper ring 124) and the profile of openings 127 and the upper and lower edges of the cylindrical electrodes 113, 114 in FIG. 6.

Figure 7:
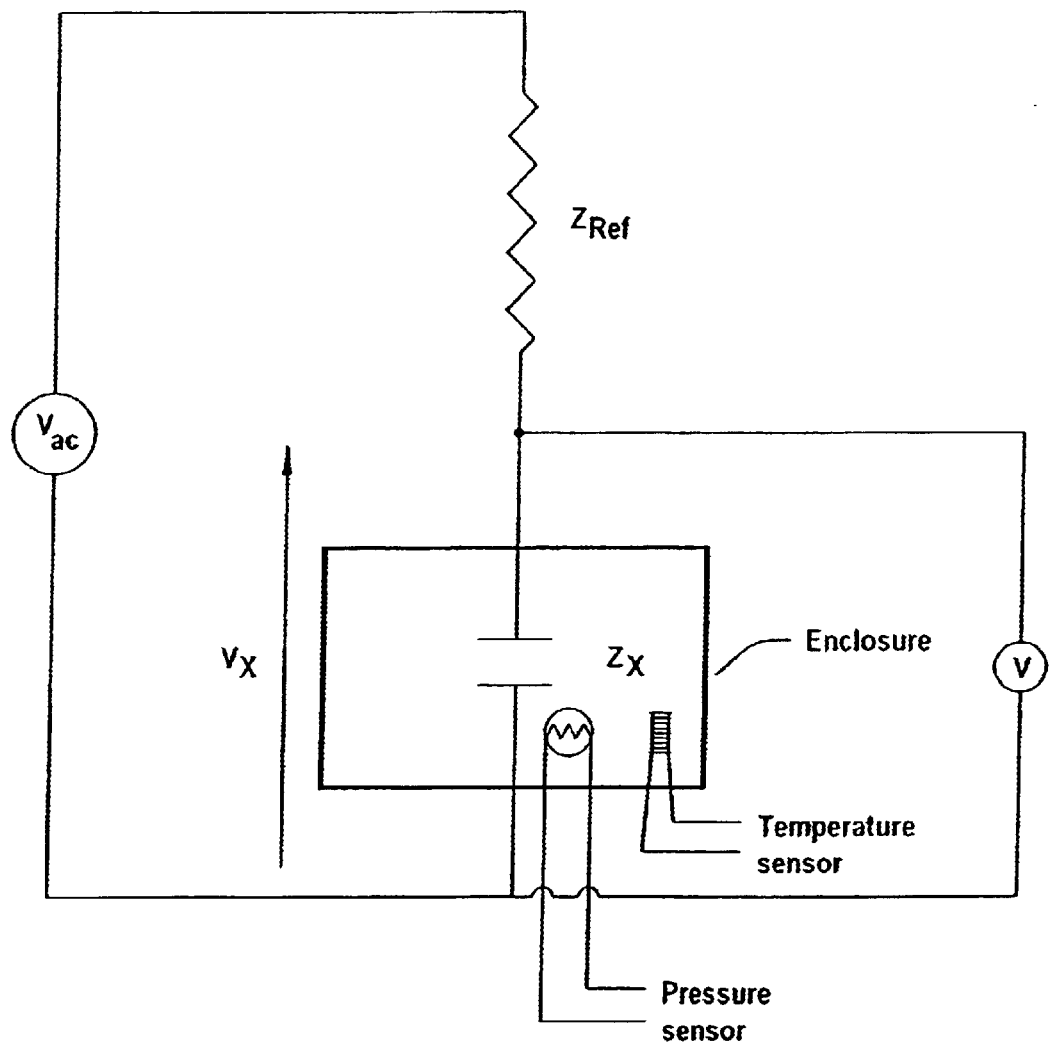
FIG. 7. is an alternative embodiment of that shown in FIG. 3 for testing gas mixtures in which the reference cell is replaced by a fixed capacitor of known impedance and in which a temperature sensor (thermocouple) and a pressure sensor are present.

FIG. 7 shows the circuitry diagram utilizing the temperature measurement necessary to adjust the preset temperature of the reference element with the actual temperature measured for the test cell. In the event that the test cell is maintained at a constant temperature corresponding to the preset temperature of the reference element by the use of circulation of the fluid mixture with thermostatic control as described below, the temperature measurement of the test cell is not necessary.

An optional pressure sensor is used as shown in FIG. 7 for the purpose of determining the pressure of a gas mixture being tested in the test cell, in which event the reference capacitor, Z, has been based on a reference cell containing a gaseous mixture in which the optimal pressure has been determined in addition to the temperature of the gas mixture and the ratio of the two gas components, measured in terms of the ratio of the methanol to the mixture of methanol and steam. The test cell used in FIG. 7 has substantially the same construction as the test cell, including the electrodes and its positioning of its compartment within the enclosure, as in the sensor embodiments of FIGS. 2a, 2b and 2c and FIGS. 6, 6a and 6b. The temperature and pressure sensors extend through the lateral walls of the electrical housing as illustrated in the embodiment of FIG. 6, into the fluid mixture contained in the enclosure. Of course, the liquid levels within the enclosure 7 shown in FIGS. 2a and 2b would not apply to the gas mixture embodiments.

When a gas mixture is tested, it is generally necessary also to take into account the pressure of the mixture, as can be achieved by the pressure sensor shown in FIG. 7 as discussed above. As shown in pages 10-95, 10-96, 10-99, 10-100, 10-101 and 10-110 of LANGE'S HANDBOOK OF CHEMISTRY, edited by John DEAN (1985 edition), the values for dielectric constant for gases can be determined on the basis of different conditions of temperature and pressure by the equation:

$$\frac{(\varepsilon - 1)_{t,p}}{(\varepsilon - 1)_{20°, 1 atm}} = \frac{p}{760[1 + 0.003411(t - 20)]}$$

This equation is indicated to be extremely accurate (error not to exceed 0.02%) in the pressure range of 700–800 mm Hg and a temperature range of 10° C. to 30° C. for gases. According to the U.S. Department of Energy report, referred to above, page 127, FIG. 5.2.3-1, the pressure in the reformer is about 30 psig. According to page 122, the general steam to methanol ratio in the vaporizer feeding the reformer would be between about 1.3 and 2.0 at flow rates sufficient to power a 10 KW fuel cell. Page 122 also indicates that the equilibrium methanol concentration in the water/methanol liquid phase feeding the vapor phase mixture is approximately one percent. It is believed that the described data should enable appropriate operation of such a system with the control sensor and process for determining the ratio of methanol to water within the degree of accuracy required by the present invention.

Based on the known dielectric constant for gases such as gaseous methanol and water, tables similar to the data shown in FIGS. 1 and 5 should be possible for such other gas mixtures at specified pressure ranges.

Although the relative impedances, and thus the capacitances (converted to dielectric constants) of the test cell in comparison to the reference cell are shown in the above specific embodiments as being determined by the ratio of the voltage of the voltage source to the voltage drop across the test cell, the ratio of the impedances could also be determined by directly measuring the voltages across the test cell and across the reference cell or by determining the ratio of the voltage source to the voltage drop across the reference cell. However, it is more convenient to take account of the known voltage of the voltage source and to measure only the voltage across the test cell. Suitable correlation of the data provides the impedance of the reference cell.

Although the present invention is primarily directed to the use of the sensor for determining the ratio of components in a liquid or gas methanol/water mixture, the sensor of the invention can also be used with respect to other fluid mixtures which have a linear and monotonic relation between the dielectric constant of the fluid mixture being tested and the weight ratio of one component in the mixture to the mixture of the two components. The operation of the sensor and method of the present invention can also be assisted by further means not specifically described. For example, as referred to above, the temperature of the fluid within the enclosure and the test cell can be thermostatically controlled by a heat sensor positioned within the enclosure containing the fluid communicating with the test cell, said heat sensor controlling heat or coolant, respectively, supplied to heating or cooling coils in said enclosure and contacting said fluid. Circulation means, such as a rotary vane, within the enclosure can assist in maintaining the fluid within the enclosure at a substantially uniform temperature.

It is understood that the specific embodiments of the sensor and methods of the invention as described herein are subject to variations in dimensions, components and operating conditions as necessary for commercial production of the sensors and practice of the process. If the sensor is to be placed within the bottom portion of the enclosure of an electrically heated vaporizer for receiving liquid water and methanol and for feeding the vaporized mixture to a reforming reactor, as described on pages 121 and 122 of the Department of Energy report acknowledged above, the sensor should have outer dimensions to fit within said bottom part. A level device is provided within the enclosure of said vaporizer to insure that the liquid level in said enclosure is always above the level of the sensor to keep it submerged.

What is claimed is:

1. A process for testing a fluid mixture containing methanol and water in a given ratio so as to determine said ratio, which comprises:

establishing a test cell between opposed electrodes contacting said fluid mixture, said fluid mixture being tested at a given temperature and said test cell being in open flow communication with said fluid mixture being tested;

imposing an alternating voltage of a given frequency across said electrodes;

measuring the dielectric response of the fluid mixture in said test cell at said temperature and frequency, providing a reference cell established by opposed electrodes having operational characteristics equivalent to those of the electrodes of the test cell and containing therebetween a fluid mixture having a known ratio of methanol to water;

wherein one of the opposed electrodes of the test cell and one of the opposed electrodes of the reference cell are respectively connected to opposite poles of a source of the alternating voltage and the other electrodes of the opposed electrodes of each of said cells are connected so that the electrodes of said cells are in series, the impedance of the test cell being determined in relation to that of the reference cell at a given voltage and frequency of the voltage source so as to compare the respective dielectric responses of said cells;

maintaining said fluid mixture of said reference cell at the same temperature as the fluid mixture being tested, said electrodes of the reference cell being subject to an alternating voltage of the same frequency as imposed on the electrodes of the test cell, measuring the dielectric response of the reference cell; and comparing said dielectric response measured in said reference cell to that measured in the test cell so as to determine the ratio of the methanol to water in the fluid mixture in the test cell.

2. A process according to claim 1, which the fluid mixture is a liquid mixture.

3. A process according to claim 2, wherein the electrodes of the test cell are substantially totally immersed in the liquid mixture.

4. A process according to claim 1, wherein the dielectric response of the test cell is measured in terms of the dielectric constant of the fluid mixture in said cell, the dielectric response of the fluid mixture being tested varying in an essentially linear and monotonic relation to the ratio of methanol to water in said mixture at a given temperature of said fluid.

5. A process according to claim 1, in which the fluid mixture of the reference cell has a ratio of methanol to water corresponding to a desired value.

6. A process according to claim 1 wherein the voltage drop across the electrodes of the test cell is determined in relation to the voltage drop across the electrodes of the reference cell so as to determine the respective impedances of said cells, the capacitive components of said impedances being correlated with the dielectric constants of the fluid mixture being tested and that of the reference cell.

7. A process according to claim 1, which comprises providing a reference element of given impedance, said impedance being equivalent to that of a reference cell having equivalent operating characteristics to those of the test cell, said reference cell having a fluid mixture of methanol and water of a known ratio and of known temperature and being operated at the same frequency as that of the test cell, and which further comprises:
 measuring the temperature of the fluid mixture being tested,
 measuring the impedance of the fluid mixture in the test cell,
 comparing the impedance of the test cell to that of the reference element so as to determine the capacitance of the test cell, and
 determining the ratio of methanol to water in the fluid mixture of the test cell on the basis of the capacitance and temperature of the mixture in the test cell.

8. A process according to claim 7, in which the fluid mixture is a liquid mixture.

9. A process according to claim 1, in which the fluid mixture being tested is being supplied to a reformer reactor for producing hydrogen.

10. A process according to claim 1, in which the dielectric response of the fluid mixture is measured substantially continuously.

11. A process for testing a fluid mixture containing methanol and water in a given ratio so as to determine said ratio, which comprises:
 establishing a test cell between opposed electrodes contacting said fluid mixture, said fluid mixture being tested at a given temperature and said test cell being in open flow communication with said fluid mixture being tested;
 imposing an alternating voltage of a given frequency across said electrodes;
 measuring the dielectric response of the fluid mixture in said test cell at said temperature and frequency, and
 wherein the fluid mixture is a gas mixture;
 providing a reference element of given impedance, said impedance being equivalent to that of a reference cell having equivalent operating characteristics to those of the test cell, said reference cell having a gas mixture of methanol and water of a known ratio and of a known temperature and pressure and being operated at the same frequency as that of the test cell, and which further comprises:
 measuring the temperature and pressure of the gas mixture being tested,
 measuring the impedance of the gas mixture in the test cell, comparing the impedance of the test cell to that of the reference element so as to determine the capacitance of the test cell, and
 determining the ratio of methanol to water in the test cell on the basis of the capacitance, temperature and pressure of the gas mixture in the test cell.

12. A sensor for determining the ratio of two components in a test fluid mixture, mixtures with different ratios of said components having respectively different dielectric constants at a given frequency of an imposed alternating voltage and at a given temperature of said test fluid mixture when said test fluid mixture is subjected to said alternating voltage, said sensor comprising:
 a first pair of opposed electrodes establishing therebetween a test cell, the opposed electrodes of said test cell being in contact with said test fluid mixture being tested, said test cell having a test cell impedance;
 a reference cell established by a second pair of opposed electrodes having equivalent operating characteristics to those of the first pair of opposed electrodes, said reference cell containing a reference fluid mixture of the two components in a known ratio and being isolated from said test fluid mixture, said reference cell having a reference cell impedance;
 an electrical circuit wherein one of the opposed electrodes of the first pair of electrodes is connected to one pole of a source of alternating voltage and one of the electrodes of the second pair of electrodes is connected to the other pole of the source of alternating voltage, and wherein the other of the opposed electrodes of the first and second pair of electrodes are connected together for serial flow between said pairs of electrodes of the test cell and reference cell, respectively; and
 a voltage measuring device connected to said circuit for measuring the voltage drop across the test cell so as to determine the voltage drop across the test cell in relation to the voltage drop across the reference cell;
 said relative voltage drops being used to determine said test cell impedance relative to said reference cell impedance and thus to determine the dielectric constant of the test fluid mixture relative to that of the reference fluid mixture at a given temperature of said test and reference fluid mixtures and at a given voltage of the imposed alternating voltage, whereby the ratio of said components of the test fluid mixture to the ratio of the components of the reference fluid mixture is correlated with the respective dielectric constants of said test and reference fluid mixtures.

13. A sensor according to claim 12, in which the electrical circuit acts as a capacitance divider circuit to determine the capacitances of the respective cells.

14. A sensor according to claim 12, in which the test cell is contained in an enclosure containing the mixture of two fluid components being tested.

15. A sensor according to claim 12, in which the opposed electrodes of the test cell are contained in an enclosure having a mixture of two liquids being tested.

16. A sensor according to claim 15, in which the opposed electrodes of the test cell are positioned so as to be totally immersed in the mixture of liquids in the container and the opposed electrodes of the reference cell are positioned to be totally immersed in the liquid mixture in the reference cell.

17. A sensor according to claim 12, which comprises:
compartment walls defining a compartment for the test cell, said compartment walls including an opening communicating with the interior of an enclosure containing the fluid being tested,
said walls further defining an adjacent compartment for the reference cell, said compartment not having an opening communicating with the interior of the enclosure containing the fluid being tested, there being a common wall separating said compartments,
said compartments, being in effective heat exchange relationship with the fluid being tested so as to maintain the fluids within the test cell and within the reference cell at substantially the same temperature.

18. A sensor according to claim 17, wherein the common wall is provided by a common electrode for both compartments, each of said pairs of opposed electrodes of the test cell and reference cell, respectively, including the common electrode, and the other electrode of each of at least the pair of opposed electrodes defining the reference cell having an exposed outer surface in contact with the fluid in the enclosure, whereby said exposed surface provides heat exchange with the fluid mixture being tested.

19. A sensor according to claim 12, in which the opposed electrodes are parallel plates.

20. A sensor according to claim 12, in which the opposed electrodes are coaxial cylinders.

21. A sensor for determining the ratio of two components in a test fluid mixture, mixtures with different ratios of said components having given dielectric constants at a given frequency of an imposed alternating voltage and at a given temperature of said test fluid mixture when said test fluid is subjected to said alternating voltage, which comprises:
a pair of opposed electrodes establishing therebetween a test cell, the opposed electrodes of said test cell being in contact with said test fluid, said test cell having a test cell impedance;
a reference element including a capacitor having two terminals, said reference element having a known impedance, said impedance being the same as that of a reference cell of equivalent operating characteristics to those of the test cell, said reference cell having a reference fluid mixture of the same two components in a known ratio and at a specific temperature;
an electrical circuit wherein one of the opposed electrodes of the test cell is connected to one pole of a source of alternating voltage of a given frequency and one of the terminals of the capacitor is connected to the other pole of the source of alternating voltage, and the other of the opposed electrodes and the other terminal of the capacitor are connected together for serial flow between the test cell and the capacitor;
a temperature measuring device for measuring the temperature of the mixture in the test cell; and
a voltage measuring device connected to said circuit for measuring the voltage drop across the test cell so as to determine the voltage drop across the test cell in relation to the voltage drop across the capacitor;
said relative voltage drops being used to determine said test cell impedance relative to said capacitor impedance and thus to determine the dielectric constant of the test fluid mixture relative to that of the reference fluid mixture at a given temperature of said test fluid mixture as determined by the temperature measuring device, and at a given voltage of the imposed alternating voltage, whereby the ratio of said components of the test fluid mixture to the ratio of the components of the reference fluid mixture is correlated with the respective dielectric constants of said test and reference fluid mixtures.

22. A sensor according to claim 21, in which the test cell is contained in an enclosure containing a mixture of two fluid components being tested.

23. The sensor according to claim 22, in which the enclosure contains a mixture of two gaseous components being tested, and which includes a pressure measuring device for measuring the pressure of the gaseous mixture in the test cell, the ratio of the two gas components in the test cell being determined on the basis of the impedance of a gas mixture in the test cell and the impedance of the reference element and the temperature and pressure of said gas mixture as measured by the temperature measuring device and pressure measuring device, respectively, the impedance of the reference cell element being the same as that of a reference cell of equivalent operating characteristics as those of the test cell, said reference cell having a gas mixture of the same two components in a known ratio and at a specific temperature and pressure.

24. A sensor according to claim 21, in which the opposed electrodes of the test cell are contained in an enclosure having a mixture of two liquids being tested and are positioned as to be totally immersed in said liquid mixture.

25. A sensor according to claim 21, in which the opposed electrodes are parallel plates.

26. A sensor according to claim 21, in which the opposed electrodes are coaxial cylinders.

27. A sensor according to claim 26, in which the cylindrical electrodes are radially spaced from each other by respective electrically insulating means adjacent the opposite ends of said cylindrical electrodes to form an annular space for the flow of the fluid being tested, said insulating means including passageways to permit the flow of said fluid.

28. A process for testing a fluid mixture containing methanol and water in a given ratio so as to determine said ratio, which comprises:
establishing a test cell between opposed electrodes contacting said fluid mixture, said fluid mixture being tested at a given temperature and said test cell being in open flow communication with said fluid mixture being tested;
imposing an alternating voltage of a given frequency across said electrodes;
measuring the dielectric response of the fluid mixture in said test cell at said temperature and frequency;
providing a reference cell established by opposed electrodes having operational characteristics equivalent to those of the electrodes of the test cell and containing therebetween a fluid mixture having a known ratio of methanol to water;
maintaining said fluid mixture of said reference cell at the same temperature as the fluid mixture being tested, said electrodes of the reference cell being subject to an alternating voltage of the same frequency as imposed on the electrodes of the test cell;
measuring the dielectric response of the reference cell; and
comparing said dielectric response measured in said reference cell to that measured in the test cell so as to determine the ratio of the methanol to water in the fluid mixture in the test cell, wherein one of the opposed electrodes of the test cell and one of the opposed electrodes of the reference cell are respectively connected to opposite poles of a source of the alternating voltage and the other electrodes of the opposed electrodes of each of said cells are connected so that the electrodes of said cells are in series, the impedance of the test cell being determined in relation to that of the reference cell at a given voltage and frequency of the voltage source so as to compare the respective dielectric responses of said cells.

29. A process according to claim 28, wherein the voltage drop across the electrodes of the test cell is determined in relation to the voltage drop across the electrodes of the reference cell so as to determine the respective impedances of said cells, the capacitive components of said impedances being correlated with the dielectric constants of the fluid mixture being tested and that of the reference cell.

* * * * *